Figure 1:
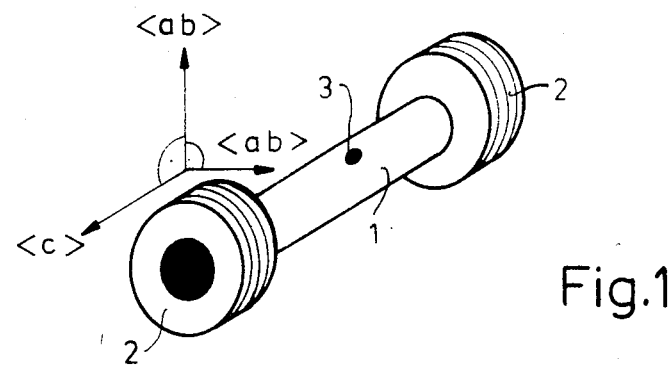

United States Patent [19]

Lersmacher

[11] Patent Number: 4,579,451
[45] Date of Patent: Apr. 1, 1986

[54] TUBULAR CUVETTE FOR ATOMIC ABSORPTION SPECTROMETRY

[75] Inventor: Bernhard Lersmacher, Aachen, Fed. Rep. of Germany

[73] Assignee: U.S. Philips Corporation, New York, N.Y.

[21] Appl. No.: 541,818

[22] Filed: Oct. 13, 1983

[30] Foreign Application Priority Data

Oct. 23, 1982 [DE] Fed. Rep. of Germany ....... 3239253

[51] Int. Cl.$^4$ .......................... G01N 21/03; G01J 3/42
[52] U.S. Cl. ...................................... 356/244; 356/312
[58] Field of Search ................................ 356/244, 312

[56] References Cited

U.S. PATENT DOCUMENTS

| | | | |
|---|---|---|---|
| 3,862,805 | 1/1975 | Tamm et al. | 356/244 |
| 3,893,769 | 7/1975 | Woolley | 356/312 |
| 3,895,873 | 7/1975 | Dennison et al. | 356/312 |
| 4,022,530 | 5/1977 | Braum et al. | 356/312 |
| 4,082,460 | 4/1978 | Braum et al. | 356/244 X |
| 4,176,956 | 12/1979 | Tomoff et al. | 356/244 X |
| 4,202,628 | 5/1980 | Koizumi et al. | 356/312 |
| 4,204,769 | 5/1980 | Lermacher et al. | 356/312 X |
| 4,338,358 | 7/1982 | Lermacher et al. | 427/242 X |

FOREIGN PATENT DOCUMENTS

| | | | |
|---|---|---|---|
| 0089079 | 9/1983 | European Pat. Off. | 356/244 |
| 2419936 | 11/1975 | Fed. Rep. of Germany | 356/312 |
| 2949476 | 6/1981 | Fed. Rep. of Germany | 356/312 |

Primary Examiner—John E. Kittle
Assistant Examiner—Mukund J. Shah
Attorney, Agent, or Firm—Paul R. Miller

[57] ABSTRACT

A cuvette for atomic absorption spectrometry includes a tube of pyrolytic graphite, electrographite or vitreous carbon with flanges provided at the ends of the tube, or in the proximity thereof, and having a common envelope of pyrolytic graphite. The flanges consist of solid layers of pyrolytic graphite in which the layer planes of the pyrolytic graphite are either directed perpendicularly to the longitudinal axis of the tube, or extend everywhere parallel to the longitudinal axis and the surface of the tube. Cuvettes with flanges having an orientation of the solid layer planes directed perpendicularly to the longitudinal axis of the tube are considered and operate as "fast", whereas those having an orientation extending everywhere parallel to the longitudinal axis are considered.

15 Claims, 4 Drawing Figures

TUBULAR CUVETTE FOR ATOMIC ABSORPTION SPECTROMETRY

The invention relates to a tubular cuvette for atomic absorption spectrometry (AAS) having flange-shaped or flange-like parts at the tube ends or in the proximity thereof with the tube and the flange-shaped or flange-like parts being provided with a common envelope of pyrolytic graphite.

The flange-shaped or flange-like parts are hereinafter also termed "flanges" or "contact rings". As materials for the flanges, electrographite, vitreous carbon as well as high-melting-point metals are suggested in U.S. patent application Ser. No. 473,518, while pyrolytic graphite is suggested as a material for the tube.

In further development of this type of cuvette, in particular in investigations of the thermal and electrical loading capacity as well as life under substantially practical conditions, it has been found in the present application that cuvettes of this type have some advantages and particular properties when the annular flanges are manufactured from solid pyrolytic graphite—hereinafter also termed pyrographite. In accordance with the layer structure of highly oriented pyrographite two possibilities of manufacturing the flanges are preferred. Namely, (a) the planes of the layers of the flanges are oriented so as to be perpendicular to the longitudinal axis of the cuvette tube—so-called radial stratifications—and (b) the planes of the layers of the flanges are oriented to extend everywhere parallel to the cuvette axis and cuvette surface, respectively, so the cuvette tube is surrounded annularly by planes of the layers—so-called azimuthal or tangential stratification.

"Radial" is to be understood to mean that the orientation of the layers is such that the vectors of good thermal and electrical conductivity of the flanges are directed radially to the cuvette axis. In the case of the "tangential" or "azimuthal" stratification the same vectors are directed parallel to the cuvette axis.

In the course of a series of experiments it was established as a matter of fact that the two embodiments according to the invention result in cuvettes which partly in their operational behaviour distinguish from each other to an unexpectedly high extent. This applies in particular to their heating and cooling behaviour as well as to the nature of the temperature distribution and the variation thereof in time along the cuvette axis.

Figure 2:
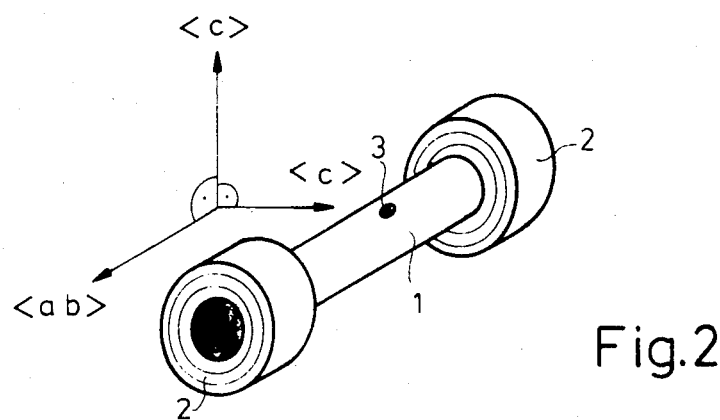
Figure 3:
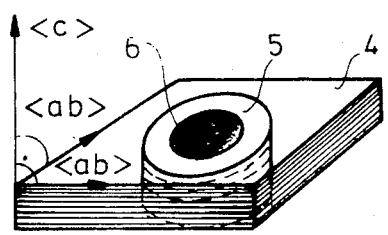
Figure 4:
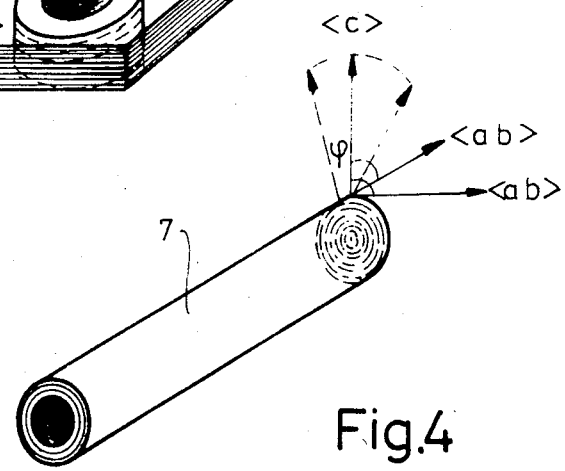

The invention will now be described in greater detail with reference to the drawing figures and a few embodiments. The drawings are perspective views of:

FIG. 1 a tubular cuvette having a flange of pyrographite in a radial stratification, FIG. 2 a tubular cuvette having a flange of pyrographite in azimuthal or tangential stratifications, FIG. 3 a workpiece of solid pyrographite for the manufacture of annular flanges with radial stratification, and FIG. 4 a workpiece of solid pyrographite for the manufacture of annular flanges having azimuthal and tangential stratifications, respectively.

FIGS. 1 and 2 show a basic tube 1 of pyrolytic graphite which contacts rings 2 of pyrolytic graphite at the ends. The tube 1 comprises a sample feed inlet 3. The assembly is covered with an envelope (not shown) of pyrolytic graphite.

FIGS. 1 to 4 furthermore show the crystallographic axes of the purolytic graphite in which the arrows indicated by <a b> indicate the position of the base planes of the graphite (0002) and the arrows indicated by <c> indicate the direction at right angles thereto, or the position of the crystallographic c-axes of the hexagonal graphite crystal. In FIG. 4 the angular distribution of the x-axes which extends over the whole $2\pi$-range (0° ... 360°) is indicated by $\Delta\phi$.

As a starting material, flanges having a radial orientation require thick-walled pyrographite which is as flat as possible (FIG. 3) from which flat plates 4 of the desired thickness are first manufactured by machining (grinding) at right angles to the stratification, and then further processing the plates—preferably by circular grinding—to discs 5 and by providing a central aperture 6 for receiving the cuvette tubes, and then further processed to the desired flange ring size.

As a starting material for flanges having azimuthal (tangential) stratification are suitable sufficiently thick-walled tubes 7 (FIG. 4) of pyrographite. These tubes are manufactured by prolonged deposition from the gaseous phase on a cylindrical mandril which consists of a high-melting-point (M.P.$\geq$2300 K.) material having a coefficient of thermal expansion as high as possible (for example, electrographite, vitreous carbon, tantalum, tungsten). After having been taken off of the substrate mandrils, the tubes are further processed to the desired size of the annular flanges by cutting, drilling, circular grinding and surface grinding.

In all of the process steps, destruction by delamination of the pyrographite parts must be and can be prevented by auxiliary measures. For a snug fit of the flange rings the conditions, as suggested in U.S. patent application Ser. No. 473,518 which is incorporated for reference purposes, must hold. The connection of flanges 2 and the basic tube 1 is also carried out in the manner described there by enveloping stratifications in layer thicknesses of approximately 10 to 100 $\mu$m, preferably 20 $\mu$m.

Parallel to the stratification the pyrographite flanges have a comparatively low resistivity of $\rho_{\parallel} = 1.8$ to $4.5 \times 10^{-4} \Omega$ cm. ($\parallel$ indicating parallel). Although this is a factor 100 times higher than that of copper, it is a factor 10 times lower than that of electrographite. Flanges of solid pyrographite in the radial orientation (a) in combination with a thin-walled cuvette tube produce a comparatively rapid heating of the latter where the strongest rise in temperature occurs in the center of the cuvette (or at the area of the sample to be analyzed), and hence, the highest temperature is reached there. On the other hand, after switching off the electric supply, a comparatively rapid cooling occurs due to the high thermal conductivity parallel to the stratification ($\lambda_{\parallel} = 3.2$ W/cm K., i.e. $\approx \lambda$ copper=3.98 W/cm K.), which in particular in series analyses is generally highly desired.

In pyrographite flanges having azimythal stratification (b) on the contrary, a completely different heating and cooling characteristic is to be observed. Since the specific resistivity $\rho_{\perp}$ is a factor 100 to 1000 times higher (dependent on the perfection of the structure) than $\rho_{\parallel}$, the conversion of the electrical energy into thermal energy preferably takes place in the flanges. ($\perp$ indicating perpendicular, $\parallel$ parallel). This has for a result that a high temperature is built up at the flanges which, depending on the orientation of the layers, expands more rapidly or more slowly, to the center of the cuvette, or towards the location of the sample. This specific behaviour may be of importance for certain analyses when the high temperature fronts approaching each other from the ends prevent condensation of the sample substances, to be analysed, at the—in the normal case—colder ends, and in addition produce a concentration of the substance to analysed in the center of the cuvette. This behaviour is further favoured by the very low thermal conductivity perpendicular to the layer ($\lambda_\perp = 0.03$ W/cm K.). The flange of orientation (b) thus forms an active heat flow barrier which is accompagnied by a correspondingly slow cooling. Hence the cuvettes having flanges of the orientation (a) may be denoted as "fast", those with the orientation (b) may be denoted as "inert".

Moreover, in both types the observation has been made that also under extreme conditions, i.e. after a few thousand pulse-like loads with each 10 to 15 kW·s, at maximum temperatures of $T_{max} = 2400$ K. to 2800 K. were achieved, no damage whatsoever at the flange cuvettes was observable. In contrast herewith—with comparable loads—damage to electrographite flanges can often be observed, such as splitered parts, cracks, working loose from the base tube. Cuvettes having flanges of pyrolytic graphite are thus mechanically more stable and hence more reliable than those having flanges of electrographite.

A number of cuvette tubes of thin-walled ($\delta$ about 350 $\mu$m) pyrolytic graphite with the dimensions 5.8 mm inside diameter/5.1 mm outside diameter, lengths 30 mm and 32 mm, were provided with solid pyrographite flanges of the two orientations described hereinbefore. The annular flanges had dimensions 10.0 mm inside diameter/5.8 mm outside diameter, width 2.0 mm. Taking into account the conductivity anisotropy of pyrolytic graphite, the following values can be calculated to a first approximation for the elextric resistances:

1. For the actual cuvette tube (resistivity $\rho_\| = 1.8$ to $4.5 \times 10^{-4} \Omega$ cm)

$$R \approx 2.0 \times 10^{-4} \times (3.0/0.06) \approx 1 \times 10^{-2} \Omega$$

2. For the flange ring having the radial (a) orientation (the same resistivity)

$$R \approx 2.0 \times 10^{-4} \times (0.2/0.503) = 0.795 \times 10^{-4} \Omega$$

3. For the flange ring having the azimuthal (b)-tangential stratification (resistivity $\rho_\perp \approx 3.5 \times 10^{-1} \Omega$ cm)

$$R = 3.5 \times 10^{-1} \times (0.2/0.503) = 1.39 \times 10^{-1} \Omega$$

Approximately the following ratios are obtained:

In flanges with radial stratification the resistance of the cuvette tube is a factor 100 times larger than that of the flanges. The energy conversion from electrical into thermal energy will thus preferably take place in the center of the cuvette. The flanges having azimuthal stratification on the contrary have a resistance with a factor 10 times higher than that of the actual cuvette tube, so the energy conversion will first and preferably take place in the flanges. The thermal resistances in the flange materials operate in the same sense. Radial orientation is equivalent to accelerated azimuthal orientation with delayed heat exchange. With the above rough calculation the complex reciprocal play of the currents from electrical and thermal energy can of course not be understood entirely—the more so because no equilibrium conditions are reached actually. However, for qualitative description of the system it is suitable, as could often be confirmed in experiment. The heating time t, for example, to a temperature of approximately 2500 K. in the center of the cuvette with otherwise the same dimensions and the same energy supply was t = 3s with radial flange orientation (a), and t = 15s with azimuthal flange orientation (b).

AAS cuvettes having flanges of pyrolytic graphite have behaved excellently in varying load tests ($n \geq 5000$ load pulses). After this load (temp.-time cycle: 12 seconds switches on, $T_{max} \approx 2800$ K.; 120 s cooling phase) the cuvettes show no damage whatsoever. By choice of the orientation of the pyrographite, on the one hand, a very "fast" cuvette can be realized in which the heating occurs most rapid in the center of the cuvette (at the area of the sample). On the other hand, an "inert" cuvette can be manufactured which, with similar good mechanical stability, is characterized in that it is heated from contact with high temperature fronts traveling towards the cuvette center within from 10 to 20 s. This type of a flange cuvette prevents "depletion" of analysis substances by evaporation at the area of the sample and condensation in the "cold" places, which cannot be avoided in usual cuvettes.

The tube consists preferably of pyrolytic graphite. According to a modified embodiment of the invention, pyrographite flanges of the type described may also be combined with basic members (cuvette tubes) of different materials, in particular of electrographite or vitreous carbon.

In a further modified embodiment of the invention the enveloping pyrographite layer provided in the poststratification at the circumference of the flange, or at the actual contact faces, is afterwards removed. This measure positively influences the energy flow, particularly in cuvettes having radially oriented flanges.

What is claimed is:

1. A tubular cuvette for atomic absorption spectrometry comprising
   a tubular member,
   flange portions provided at least in proximity with ends of said tubular member, said flange portions consisting of solid layers of pyrolytic graphite, and
   a common envelope of pyrolytic graphite covering at least said tubular member.

2. A tubular cuvette according to claim 1, wherein said common envelope covers said flange portions.

3. A tubular cuvette according to claim 2, wherein said solid layers of pyrolytic graphite are in planes perpendicular to the longitudinal axis of said tubular member.

4. A tubular cuvette according to claim 3, wherein said tubular member consists of pyrolytic graphite.

5. A tubular cuvette according to claim 3, wherein said tubular member consists of electrographite or vitreous carbon.

6. A tubular cuvette according to claim 2, wherein said solid layers of pyrolytic graphite extend parallel to the longitudinal axis and the surface of said tubular member.

7. A tubular cuvette according to claim 6, wherein said tubular member consists of pyrolytic graphite.

8. A tubular cuvette according to claim 6, wherein said tubular member consists of electrographite or vitreous carbon.

9. A tubular cuvette according to claim 1, wherein said flange portions are free of said common envelope of pyrolytic graphite.

10. A tubular cuvette according to claim 9, wherein said solid layers of pyrolytic graphite are in planes perpendicular to the longitudinal axis of said tubular member.

11. A tubular cuvette according to claim 10, wherein said tubular member consists of pyrolytic graphite.

12. A tubular cuvette according to claim 10, wherein said tubular member consists of electrographite or vitreous carbon.

13. A tubular cuvette according to claim 9, wherein said solid layers of pyrolytic graphite extend parallel to the longitudinal axis and the surface of said tubular member.

14. A tubular cuvette according to claim 12, wherein said tubular member consists of pyrolytic graphite.

15. A tubular cuvette according to claim 12, wherein said tubular member consists of electrographite or vitreous carbon.

* * * * *